US009610157B2

(12) United States Patent
Braido et al.

(10) Patent No.: US 9,610,157 B2
(45) Date of Patent: Apr. 4, 2017

(54) LEAFLET ABRASION MITIGATION

(71) Applicant: St. Jude Medical, Cardiology Division, Inc., St. Paul, MN (US)

(72) Inventors: Peter N. Braido, Wyoming, MN (US); Kent J. Smith, Shoreview, MN (US); Andrea L. McCarthy, Vadnais Heights, MN (US); Yousef F. Alkhatib, Edina, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 14/662,475

(22) Filed: Mar. 19, 2015

(65) Prior Publication Data

US 2015/0265401 A1    Sep. 24, 2015

Related U.S. Application Data

(60) Provisional application No. 61/968,527, filed on Mar. 21, 2014.

(51) Int. Cl.
*A61F 2/24* (2006.01)

(52) U.S. Cl.
CPC .............. *A61F 2/2409* (2013.01); *A61F 2/24* (2013.01); *A61F 2/2412* (2013.01); *A61F 2/2418* (2013.01); *A61F 2210/0076* (2013.01); *A61F 2220/0025* (2013.01); *A61F 2230/0069* (2013.01)

(58) Field of Classification Search
CPC ........ A61F 2/2463; A61F 2/2412; A61F 2/24; A61F 2220/0025
See application file for complete search history.

(56) References Cited

U.S. PATENT DOCUMENTS

| 3,657,744 A | 4/1972 | Ersek |
| 4,275,469 A | 6/1981 | Gabbay |
| 4,491,986 A | 1/1985 | Gabbay |
| 4,759,758 A | 7/1988 | Gabbay |

(Continued)

FOREIGN PATENT DOCUMENTS

| DE | 19857887 B4 | 5/2005 |
| DE | 10121210 B4 | 11/2005 |

(Continued)

OTHER PUBLICATIONS

Catheter-implanted prosthetic heart valves, Knudsen, L.L., et al., The International Journal of Artificial Organs, vol. 16, No. 5 1993, pp. 253-262.

(Continued)

*Primary Examiner* — David Isabella
*Assistant Examiner* — Dinah Baria
(74) *Attorney, Agent, or Firm* — Lerner, David, Littenberg, Krumholz & Mentlik, LLP

(57) ABSTRACT

A prosthetic heart valve includes a stent extending in a longitudinal direction and having a plurality of commissure features. A valve assembly is secured to the stent, the valve assembly including a cuff and a plurality of leaflets. Each of the leaflets has a pair of attachment regions and a free edge extending between the attachment regions. A deflection feature disposed in each attachment region is configured and arranged to prevent the free edges of the leaflets from contacting at least one of the stent or the cuff.

5 Claims, 10 Drawing Sheets

(56) References Cited

U.S. PATENT DOCUMENTS

| | | |
|---|---|---|
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,480,423 A | 1/1996 | Ravenscroft et al. |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,685,625 B2 | 2/2004 | Gabbay |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,311,730 B2 | 12/2007 | Gabbay |
| 7,374,573 B2 | 5/2008 | Gabbay |
| 7,381,218 B2 | 6/2008 | Schreck |
| 7,452,371 B2 | 11/2008 | Pavcnik et al. |
| 7,510,572 B2 | 3/2009 | Gabbay |
| 7,524,331 B2 | 4/2009 | Birdsall |
| RE40,816 E | 6/2009 | Taylor et al. |
| 7,585,321 B2 | 9/2009 | Cribier |
| 7,682,390 B2 | 3/2010 | Seguin |
| 7,731,742 B2 | 6/2010 | Schlick et al. |
| 7,803,185 B2 | 9/2010 | Gabbay |
| 7,846,203 B2 | 12/2010 | Cribier |
| 7,846,204 B2 | 12/2010 | Letac et al. |
| 7,914,569 B2 | 3/2011 | Nguyen et al. |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| D660,432 S | 5/2012 | Braido |
| D660,433 S | 5/2012 | Braido et al. |
| D660,967 S | 5/2012 | Braido et al. |
| D684,692 S | 6/2013 | Braido |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0210304 A1 | 10/2004 | Seguin et al. |
| 2005/0096726 A1 | 5/2005 | Sequin et al. |
| 2005/0137695 A1 | 6/2005 | Salahieh et al. |
| 2005/0137697 A1 | 6/2005 | Salahieh et al. |
| 2005/0256566 A1 | 11/2005 | Gabbay |
| 2006/0008497 A1 | 1/2006 | Gabbay |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0173532 A1 | 8/2006 | Flagle et al. |
| 2006/0178740 A1 | 8/2006 | Stacchino et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259136 A1* | 11/2006 | Nguyen ............... A61F 2/2412 623/2.18 |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0112309 A1 | 4/2009 | Jaramillo et al. |
| 2009/0138079 A1 | 5/2009 | Tuval et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2012/0197391 A1* | 8/2012 | Alkhatib ............... A61F 2/2418 623/2.18 |
| 2013/0150956 A1 | 6/2013 | Yohanan et al. |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1584306 A1 | 10/2005 |
| EP | 1598031 A2 | 11/2005 |
| EP | 1360942 B1 | 12/2005 |
| EP | 1926455 A2 | 6/2008 |
| FR | 2850008 A1 | 7/2004 |
| FR | 2847800 B1 | 10/2005 |

(56) References Cited

FOREIGN PATENT DOCUMENTS

| WO | 9117720 | A1 | 11/1991 |
|---|---|---|---|
| WO | 9716133 | A1 | 5/1997 |
| WO | 9832412 | A2 | 7/1998 |
| WO | 9913801 | A1 | 3/1999 |
| WO | 0128459 | A1 | 4/2001 |
| WO | 0149213 | A2 | 7/2001 |
| WO | 0154625 | A1 | 8/2001 |
| WO | 0156500 | A2 | 8/2001 |
| WO | 0176510 | A2 | 10/2001 |
| WO | 0236048 | A1 | 5/2002 |
| WO | 0247575 | A2 | 6/2002 |
| WO | 03047468 | A1 | 6/2003 |
| WO | 2006073626 | A2 | 7/2006 |
| WO | 2007071436 | A2 | 6/2007 |
| WO | 2008070797 | A2 | 6/2008 |
| WO | 2009149462 | A2 | 12/2009 |
| WO | 2010008548 | A2 | 1/2010 |
| WO | 2010008549 | A1 | 1/2010 |
| WO | 2010096176 | A1 | 8/2010 |
| WO | 2010098857 | A1 | 9/2010 |
| WO | 2012048035 | A2 | 4/2012 |

OTHER PUBLICATIONS

Transluminal Aortic Valve Placement, Moazami, Nader, et al., ASAIO Journal, 1996; 42:M381-M385.
Transluminal Catheter Implanted Prosthetic Heart Valves, Andersen, Henning Rud, International Journal of Angiology 7:102-106 (1998).
Transluminal implantation of artificial heart valves, Andersen, H. R., et al., European Heart Journal (1992) 13, 704-708.
Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.
U.S. Appl. No. 29/375,243, filed Sep. 20, 2010.
U.S. Appl. No. 29/375,260, filed Sep. 20, 2010.
Ruiz, Carlos, Overview of PRE-CE Mark Transcatheter Aortic Valve Technologies, Euro PCR, 2010.
Percutaneous aortic valve replacement: resection before implantation, 836-840, Quaden, Rene et al., European J. of Cardio-thoracic Surgery, 27 (2005).
International Search Report and Written Opinion for Application No. PCT/US2015/021378 dated Aug. 4, 2015.

* cited by examiner

LEAFLET ABRASION MITIGATION

CROSS-REFERENCE TO RELATED APPLICATIONS

The present application claims the benefit of the filing date of U.S. Provisional Patent Application No. 61/968,527 filed Mar. 21, 2014, the disclosure of which is hereby incorporated herein by reference.

BACKGROUND OF THE INVENTION

The present invention relates to heart valve replacement and, in particular, to collapsible prosthetic heart valves. More particularly, the present invention relates to collapsible prosthetic heart valves having unique valve leaflet attachments.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two common types of stents on which the valve structures are ordinarily mounted: a self-expanding stent and a balloon-expandable stent. To place such valves into a delivery apparatus and ultimately into a patient, the valve may first be collapsed or crimped to reduce its circumferential size and diameter.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating use site. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

BRIEF SUMMARY OF THE INVENTION

In some embodiments, a prosthetic heart valve includes a stent extending in a longitudinal direction and having a plurality of commissure features,; a valve assembly secured to the stent, the valve assembly including a cuff and a plurality of leaflets, each of the leaflets having a pair of attachment regions and a free edge extending between the attachment regions; and a deflection feature in an attachment region of a leaflet and configured and arranged to prevent the free edge of the leaflet from contacting at least one of the stent or the cuff.

In some embodiments, a prosthetic heart valve includes a stent having a collapsed condition and an expanded condition, the stent having a plurality of commissure features; a valve assembly secured to the stent, the valve assembly including a cuff and a plurality of leaflets, each of the leaflets having a pair of attachment regions and a free edge extending between the attachment regions; and at least one of a swatch of material, a leaflet tab and a cuff flap disposed adjacent the attachment regions and configured and arranged to prevent the free edge of one of the plurality of leaflets from contacting at least one of the stent or the cuff.

BRIEF DESCRIPTION OF THE DRAWINGS

Various embodiments of the present invention are described herein with reference to the drawings, wherein.

Various embodiments of the present invention will now be described with reference to the appended drawings. It will be appreciated that these drawings depict only some embodiments of the invention and are therefore not to be considered limiting of its scope.

DETAILED DESCRIPTION

The present disclosure is directed to prosthetic heart valves having deflective features coupleable to at least one of a cuff and a leaflet to reduce and/or prevent abrasion of a leaflet as well as portions of the cuff and methods of making same. Such deflective features may modify the movement of the leaflets as will be explained in greater detail below. As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. Also, as used herein, the words "substantially," "generally" and "about" are intended to mean that slight variations from absolute are included within the scope of the structure or process recited.

Figure 1A:
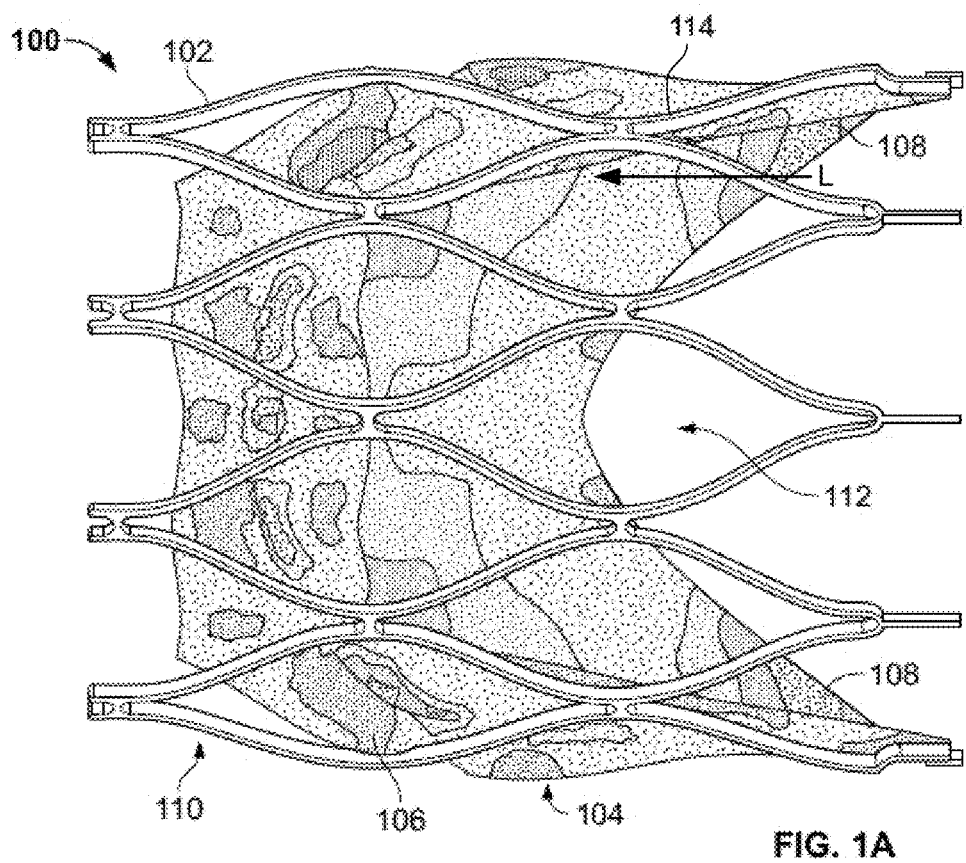
FIG. 1A is a partial side view of a prosthetic heart valve showing a potential strain distribution profile in the valve assembly.

FIG. 1A shows a typical collapsible prosthetic heart valve 100. The prosthetic heart valve 100 is designed to replace the function of the native aortic valve of a patient. Examples of collapsible prosthetic heart valves are described in International Patent Application Publication No. WO/2009/042196; U.S. Pat. Nos. 7,018,406; and 7,329,278, the disclosures of all of which are hereby incorporated herein by reference. Although the invention is described herein as applied to a prosthetic heart valve for replacing a native aortic valve, the invention is not so limited, and may be applied to prosthetic valves for replacing other types of cardiac valves.

The prosthetic heart valve 100 includes a stent or frame 102, which may be wholly or partly formed of any biocompatible material, such as metals, synthetic polymers, or biopolymers capable of functioning as a stent. Stent 102 is expandable and collapsible so that prosthetic heart valve 100 may be transitioned between a collapsed condition and an expanded condition. Suitable biopolymers include, but are not limited to, elastin, and mixtures or composites thereof. Suitable metals include, but are not limited to, cobalt, titanium, nickel, chromium, stainless steel, and alloys thereof, including nitinol. Suitable synthetic polymers for use as a stent include, but are not limited to, thermoplastics, such as polyolefins, polyesters, polyamides, polysulfones, acrylics, polyacrylonitriles, polyetheretherketone (PEEK), and polyaramides. The stent 102 may have an annulus section 110, an aortic section (not shown), and an intermediate section (not shown) disposed between the annulus and aortic sections. Each of the annulus section 110, the intermediate section, and the aortic section of the stent 102 includes a plurality of cells 112 connected to one another around the stent. The annulus section 110, the intermediate section, and the aortic section of the stent 102 may each include one or more annular rows of cells 112 connected to one another. For instance, the annulus section 110 may have two annular rows of cells 112. When the prosthetic heart valve 100 is in the expanded condition, each cell 112 may be substantially diamond shaped. Regardless of its shape, each cell 112 is formed by a plurality of struts 114. For example, a cell 112 may be formed by four struts 114.

The stent 102 may include commissure features or commissure posts (not shown) which may connect at least two cells 112 in the longitudinal direction of the stent 102. The commissure features may include eyelets that facilitate the suturing of a valve assembly and/or leaflets to the stent 102.

The prosthetic heart valve 100 also includes a valve assembly 104 attached inside the annulus section 110 of the stent 102. United States Patent Application Publication No. 2008/0228264 and United States Patent Application Publication No. 2008/0147179, the entire disclosures of both of which are hereby incorporated herein by reference, describe suitable valve assemblies. The valve assembly 104 may be wholly or partly formed of any suitable biological material, fabric or a polymer. Examples of biological materials suitable for the valve assembly 104 include, but are not limited to, porcine or bovine pericardial tissue. Examples of polymers suitable for the valve assembly 104 include, but are not limited to, fabric or polymers such as, polyurethane, ultra-high molecular weight polyethylene, polyethylene terephthalate and polyester.

The valve assembly 104 may include a cuff 106 disposed on the luminal surface of annulus section 110, on the abluminal surface of the annulus section, or on both surfaces, and the cuff may cover all or part of either or both of the luminal and abluminal surfaces of the annulus section. FIG. 1A shows cuff 106 disposed on the luminal surface of annulus section 110 so as to cover part of the annulus section while leaving another part thereof uncovered. In addition to the materials for forming valve assembly 104 noted above, the cuff 106 and/or any of the sutures described herein may include ultra-high-molecular-weight polyethylene. The valve assembly 104 may further include a plurality of leaflets 108 which collectively function as a one-way valve.

Figure 1B:
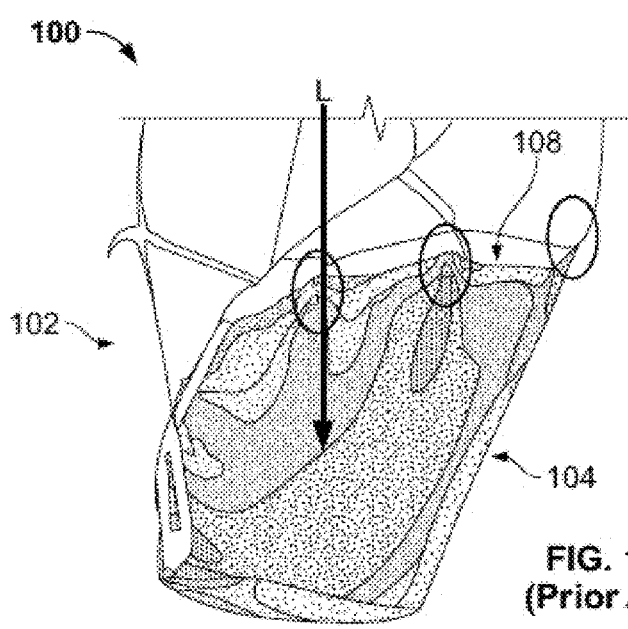
FIG. 1B is an enlarged partial view of the prosthetic heart valve of FIG. 1A showing the strain distribution in the leaflet.

The cuff 106 of the prosthetic heart valve 100 of FIG. 1A tends to experience relatively high strain and/or stress at certain locations. In such heart valves 100, the pressure of the blood that leaflets 108 keep from flowing into the left ventricle may subject leaflets 108 to a load in the direction indicated by arrow L, shown in FIG. 1B. This load may cause high stress and/or strain on the cuff and/or leaflets, particularly where they are joined to one another. Moreover, a typical load may cause the cuff and/or leaflets to wear over time. To manage the increased stress and strain on the cuff 106, some conventional prosthetic heart valves have made the cuff thicker. However, thicker cuffs generally lead to a larger heart valve in the collapsed condition that is more difficult to deliver and implant.

Figure 2:
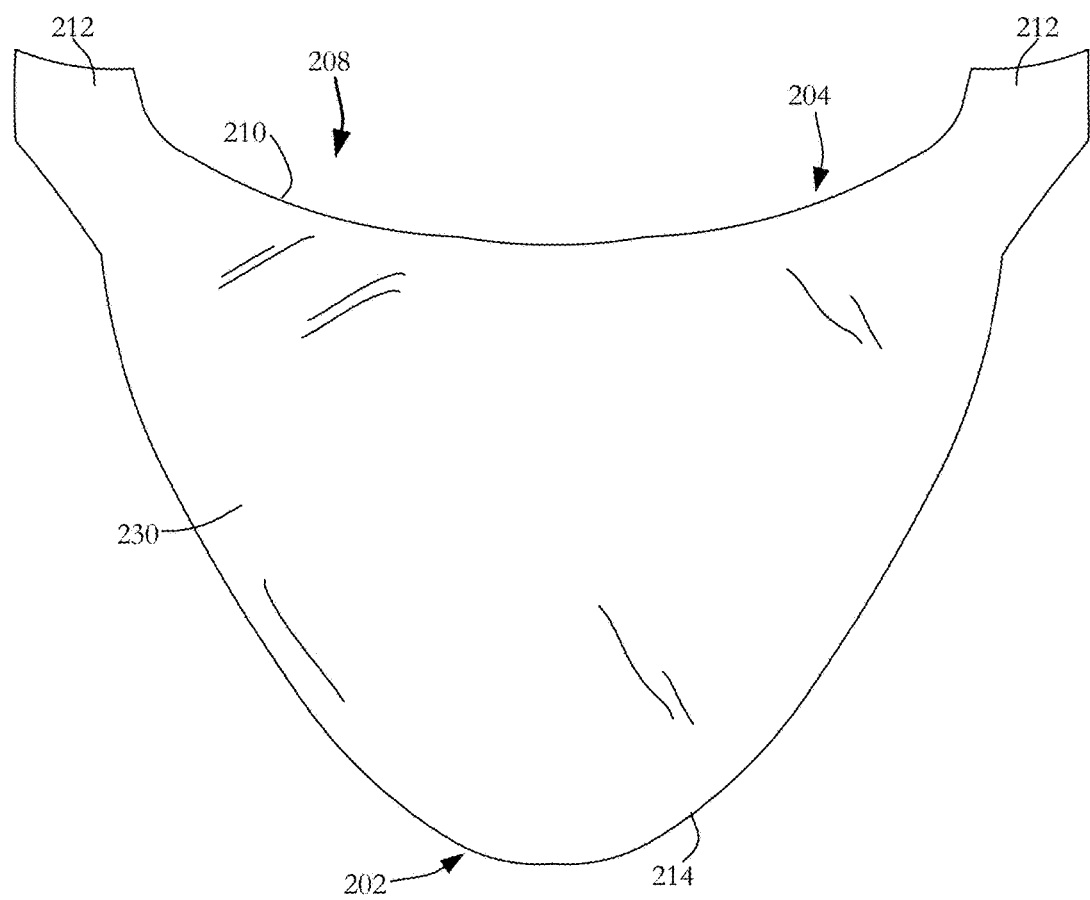
FIG. 2 is a side view of a leaflet showing regions prone to abrasion.

FIG. 2 illustrates one of several leaflets 208 that form a valve assembly. Leaflet 208 extends between proximal end 202 and distal end 204 and includes a belly 230 having a free edge 210 stretching between attachment regions 212, which couple the leaflet to the commissure features of a stent. A substantially parabolic belly contour 214 is formed between attachment regions 212 on the edge of leaflet 208 opposite free edge 210. In some examples, two leaflets 208 may be attached to each commissure feature of a stent. When the valve assembly is functioning properly, free edges 210 of leaflets 208 separate from one another to permit blood flow through the valve in one direction and coapt with one another to impede blood flow in the opposite direction. In addition to the previously described strains, as leaflets 208 of the valve assembly open and close, portions of the leaflet may repeatedly deflect and contact other anatomical features, such as calcium nodules, or features of the stent. When this occurs, abrasion may occur at any position such as at belly 230 of the leaflet or at a corresponding region of the cuff that is contacted by the leaflet. To prevent such abrasion of leaflet 208 as well as those areas of the cuff, several deflection features described below may be incorporated into leaflet 208. These deflective features may add bulk and/or stiffness to leaflet 208 to limit the deflection of the leaflet.

Figure 3A:
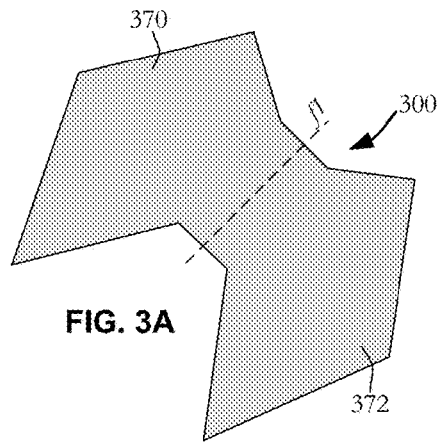
FIG. 3A is a side view of an unfolded swatch of material.

FIG. 3A is a side view of swatch 300 for modifying the movement of leaflets. Swatch 300 may be formed of tissue such as bovine or porcine tissue, a fabric or a polymer such as ultra-high-molecular-weight polyethylene, polyurethane, polyethylene terephthalate, polyester, polytetrafluoroethylene, silicone, urethane, nylon, and the like and/or combinations thereof. In a first example, swatch 300 is a strip of material having a first wing 370 and a second wing 372, the two wings being symmetric with respect to fold line f1. It will be understood, however, that the symmetry described herein and in the following embodiments is exemplary and that other configurations are possible. For example, in some variations, wings 370,372 may be asymmetric or of differing shapes and that first wing 370 may be larger than second wing 372 or vice versa.

Figure 3C:
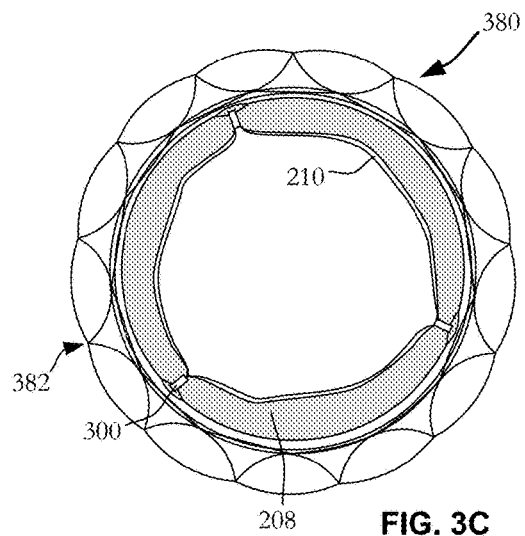
FIG. 3C is a top end view of a prosthetic heart valve having leaflets coupled via swatches.
Figure 3B:
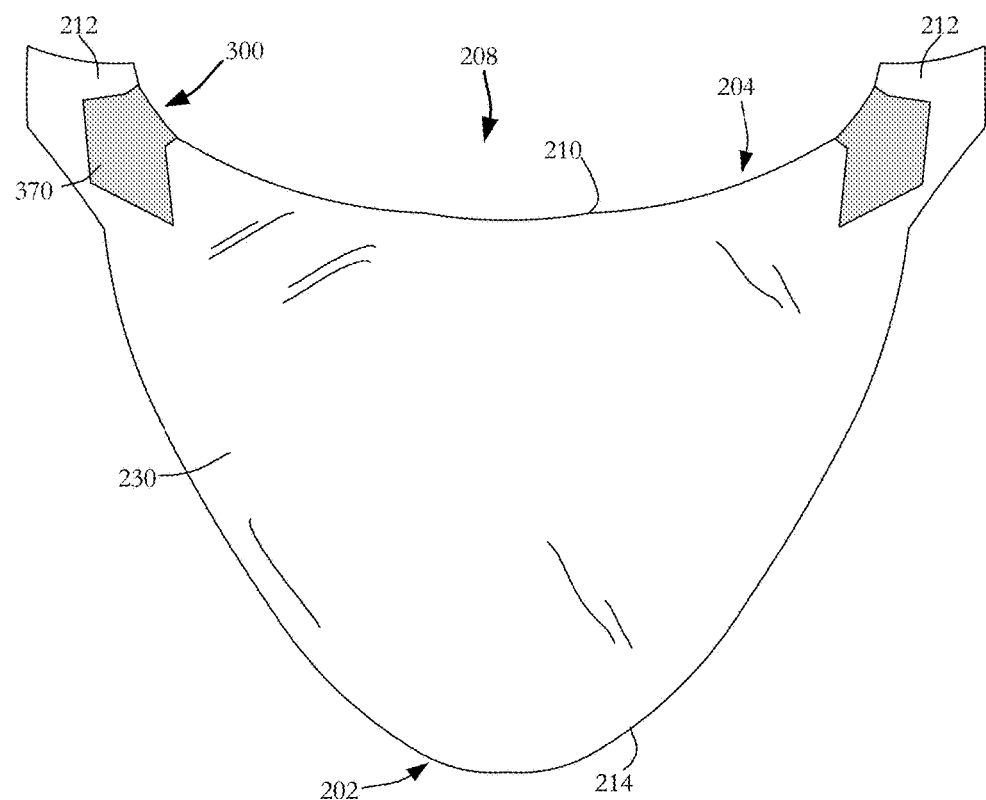
FIG. 3B is a side view of the swatch of FIG. 3A coupled to a leaflet adjacent a region at which the leaflet attaches to the valve stent.

FIG. 3B illustrates two of the swatches 300 of FIG. 3A applied to free edge 210 of leaflet 208 adjacent attachment regions 212. Though FIG. 3B illustrates swatches 300 coupled to a single leaflet 208, this is only done for clarity and it will be understood that each swatch 300 may hold two leaflets 208 together at each commissure feature. Wings 370,372 may be folded at line f1 over free edge 210 adjacent attachment regions 212 with two leaflets 208 sandwiched therebetween. Swatches 300 may be secured to two adjacent leaflets 208 using sutures, adhesive, or any suitable method to add stiffness and/or bulk near attachment regions 212. When coupled to leaflets 208, swatches 300 may space leaflets 208 from the inner surface of a stent. Thus, in the open position of leaflets, the spacing provided by swatches 300 prevent free edges 210 or other portions of leaflet 208 from opening too far to contact calcium nodules and/or other features of the stent.

FIG. 3C is a top end view of a prosthetic heart valve 380 having stent 382 coupled to leaflets 208. As seen from FIG. 3C, adjacent leaflets 208 are coupled together via swatches 300. Swatches 300 couple leaflets 208 together and limit the range of motion of free edges 210 so as to prevent contact of free edges 210 with other structures, such as calcium nodules in the native anatomy upon opening.

Figure 4A:
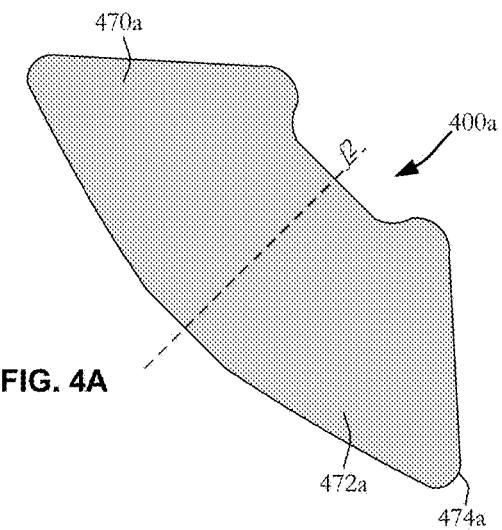
FIGS. 4A-D are side views of various configurations of swatches.

FIGS. 4A-D are side views of various other examples of swatches. FIG. 4A illustrates swatch 400a formed of a single piece of material having first wing 470a and second wing 472a. Swatch 400a is symmetric with respect to fold line f2, but wings 470a, 472a have corners 474a that are more smoothly curved than those of wings 370,372 of swatch 300. Swatch 400b of FIG. 4B includes wings 470b,472b in the form of oblong lobes joined to one another by a short neck 474. The overall shape of swatch 400b is symmetric about a fold line f3 through neck 474.

Figure 4B:
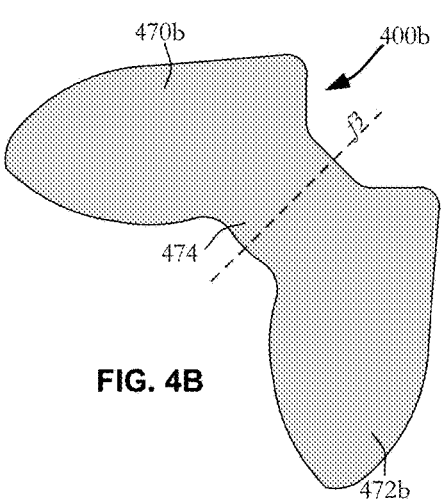
Figure 4C:
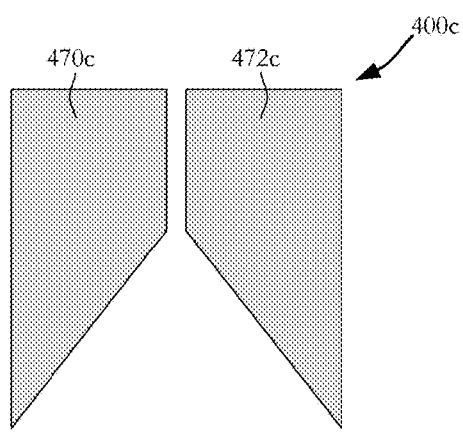
Figure 4D:
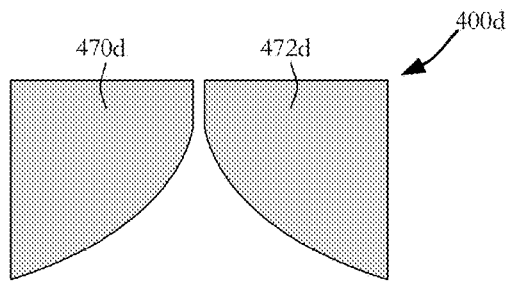

Instead of being formed of a single piece of material that is folded as shown in FIGS. 4A and 4B, the swatches may be formed of two separate pieces of material that are attached separately to the leaflets. In FIG. 4C, swatch 400c includes two separate wings 470c,472c, each having a generally rectangular shape with an angled end. In FIG. 4D, swatch 400d includes two separate wings 470d,472d that are each substantially a quadrant of a circle. It will be understood that each wing may be formed in a variety of geometric shapes such as circles, semicircles, ovals, rectangles, squares, triangles and the like, and that the examples shown herein are merely exemplary. Thus, certain configurations of the wings may be better for manufacturing, while others allow for a smaller profile.

Instead of having one or more separately formed swatches attached to the leaflets to limit the range of motion of the free edges, the leaflets may be formed with integrated deflection features. Without being bound to any particular theory, the integrated deflection features may limit the deflection of the leaflet free edge in several ways. For example, the deflection features may provide increased bulk and/or stiffness at certain regions (e.g., adjacent commissure features) so as to radially space the free edge of leaflets away from the stent and/or calcium nodules and reduce deflection of the leaflet, thereby preventing abrasion at portions of the leaflet and/or cuff. Alternatively, the integrated deflection features may shorten the length of the free edge that is capable of deflection, thereby limiting the amount of deflection.

Figure 5A:
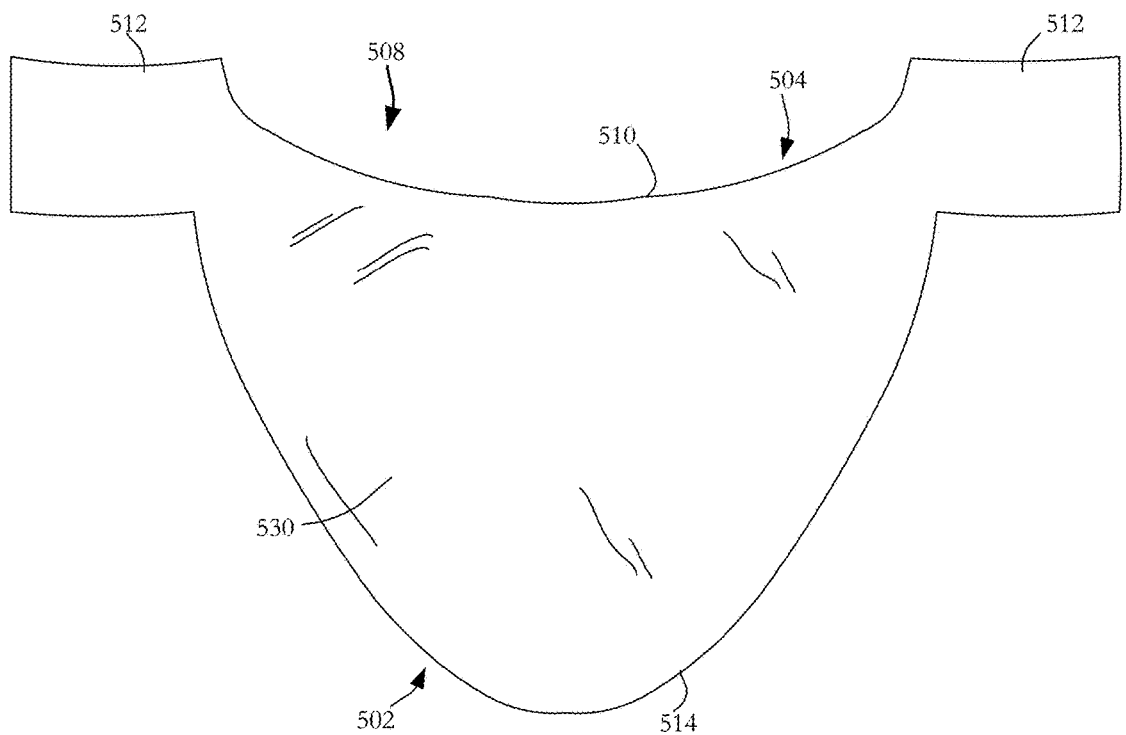
FIG. 5A is a side view of a leaflet showing an enlarged leaflet attachment region suitable for rolling.
Figure 5B:
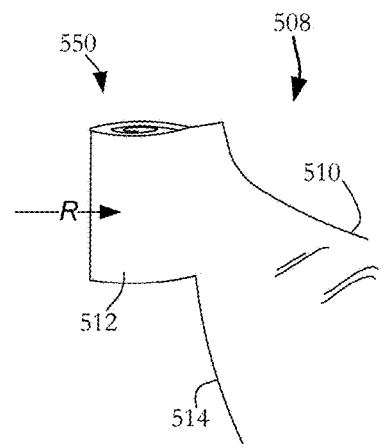
FIG. 5B is a highly schematic detailed view of the leaflet attachment region of FIG. 5A in a rolled configuration.

FIG. 5A is a side view of leaflet 508, which extends between proximal end 502 and distal end 504 and includes a belly 530 having a free edge 510 stretching between attachment regions 512, which couple the leaflet to the commissure features of a stent. A substantially parabolic belly contour 514 is formed between attachment regions 512 on the edge of leaflet 508 opposite free edge 510. As shown in FIG. 5A, attachment regions 512 are larger than attachment regions 212 of leaflet 208. The enlarged rectangular attachment regions 512 may be rolled lengthwise in the direction of arrow R to form rolled attachment region 550 in the shape of a coil, as shown in FIG. 5B. When rolled attachment region 550 is coupled to a commissure feature and/or cuff, each leaflet 508 becomes radially spaced from the stent. In at least some examples, this spacing may be between 1 mm to about 10 mm. More specifically, such a spacing may be between about 2 mm to about 6 mm. As a result, leaflets 508 will open and close but will do so at a smaller diameter such that free edge 510 will not contact the stent when opened. As a result, the rolled attachment regions limit the deflection of leaflet 508, thereby reducing abrasion.

Figure 6A:
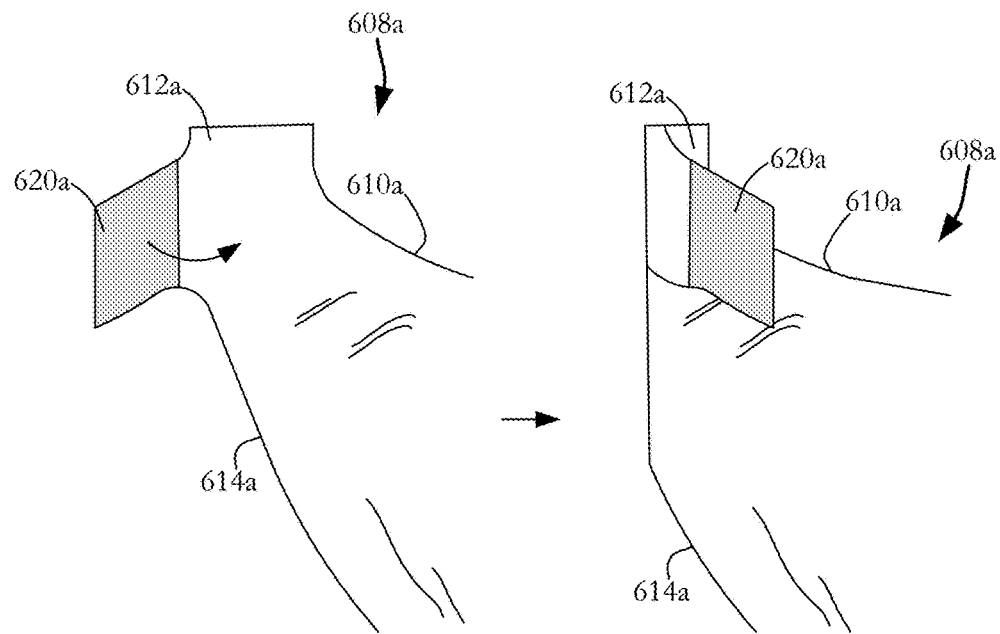
FIGS. 6A-D are highly schematic partial side views of various configurations of leaflet attachment regions in their unfolded and folded conditions.

Several variations of leaflet attachment regions are described with reference to FIGS. 6A-D. In FIG. 6A, leaflet 608a has a free edge 610a, attachment region 612a and belly contour 614a. Instead of enlarging all of attachment region 612a as shown in FIGS. 5A and 5B, each attachment region 612a may include a square tab 620a along the outer lateral edge thereof. Tabs 620a may be integrally formed with leaflet 608a or may be formed of separate pieces of tissue, fabric or polymeric sheet that are subsequently attached to leaflet 608a. Tabs 620a and/or attachment region 612a may simply be folded sideways as shown and attached to leaflet 608a, a commissure feature (not shown) or a cuff (also not shown) to limit the deflection of leaflet 608a.

Figure 6B:
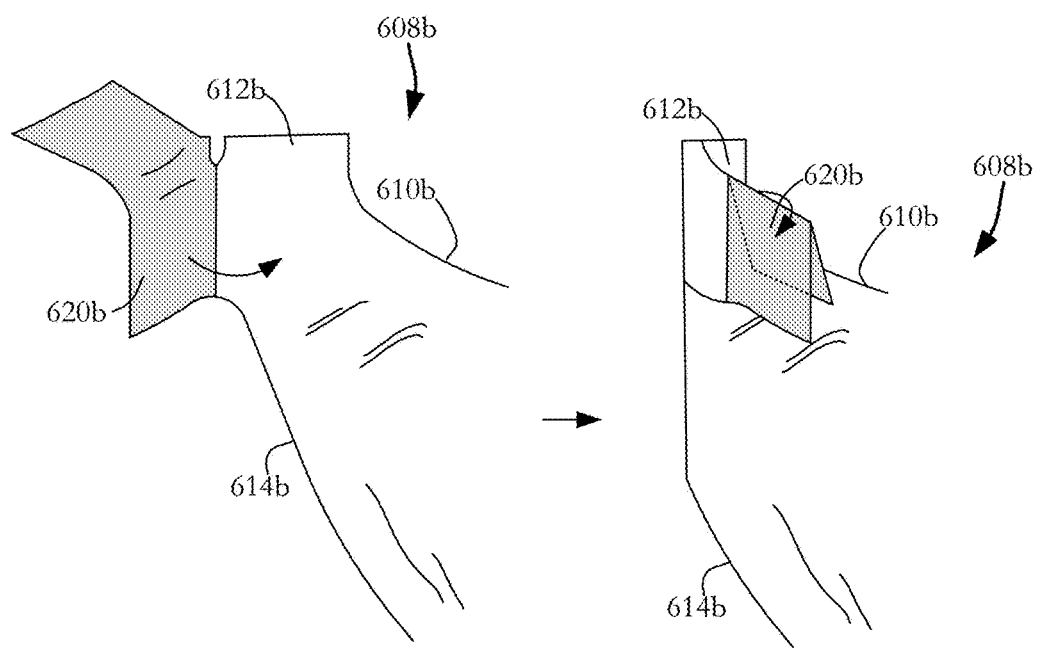

In FIG. 6B, leaflet 608b has a free edge 610b, attachment region 612b and belly contour 614b. Adjacent attachment regions 612b are elongated tabs 620b. Elongated tabs 620b may be integrally formed with leaflet 608b or may be formed of separate pieces of tissue, fabric or polymeric sheet that are subsequently attached to leaflet 608b. Tabs 620b and attachment region 612a may be folded sideways as with tabs 620a, but the upper portion of each tab 620b may be folded over the free edge of one or both leaflets at a commissure. The folded tabs may then be attached to leaflet 608b and each other to limit the deflection of leaflet 608b.

Figure 6C:
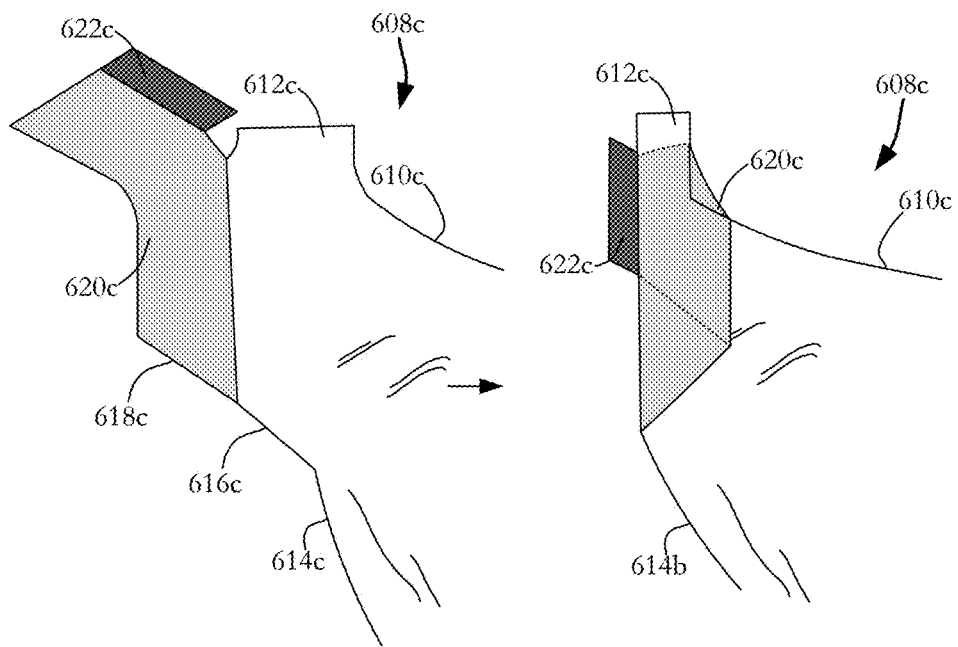

In a third variation, shown in FIG. 6C, leaflet 608c has a free edge 610c, attachment regions 612c and belly contour 614c. Attachment regions 612c each have a diagonal proximal edge 616c that merges with belly contour 614c. Tabs 620c may be joined to attachment regions 612c and include a diagonal edge 618c that may be a continuation of diagonal edge 616c. As shown, each tab 620c is substantially L-shaped with an additional segment 622c. Attachment region 612c along with tab 620C may be folded in toward free edge 610c, then 620c is folded over the free edge 610c of one leaflet and down the back side of the leaflet, so that segment 622c is substantially aligned behind attachment region 612c. The added structure of tab 620c and segment 622c when folded may provide greater bulk near the commissure feature such that the deflection of leaflet 608c is limited and so that the entire assembly is securely held together and load is properly transferred.

Figure 6D:
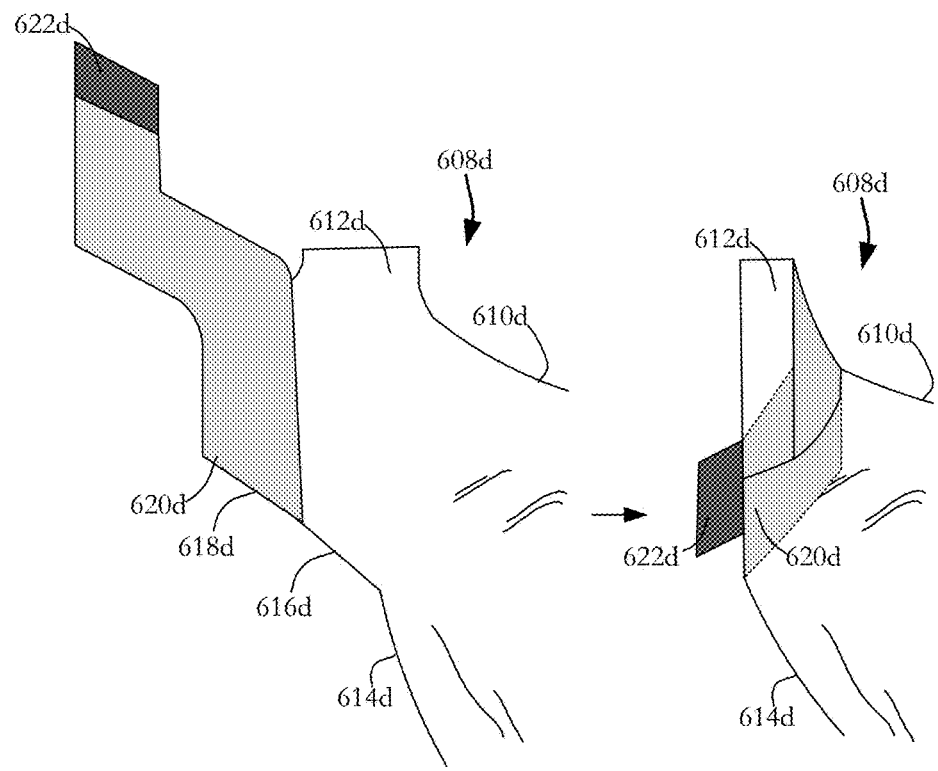

FIG. 6D shows a fourth variation in which leaflet 608d has a free edge 610d, attachment regions 612d and belly contour 614d. Each of the attachment regions 612d has a diagonal proximal edge 616d that merges with belly contour 614d. Tab 620d may be joined to attachment regions 612d and include a diagonal edge 618d that may be a continuation of diagonal edge 616d. Each tab 620c may be substantially S-shaped with diagonal edge 618d at one end of the S-shape and an additional segment 622d at the other end of the S-shape. Attachment region 612d along with tab 620D may be folded in toward free edge 610d, then then 620d is folded over the free edge 610c of both leaflets at a commissure and down the side of the adjacent leaflet so that segment 622d can be attached to the cuff or tucked behind the commissure. The added thickness supplied by folded tab 620d and segment 622d may therefore limit the deflection of leaflet 608d in a manner similar to that of leaflets 608a-c.

Figure 7:
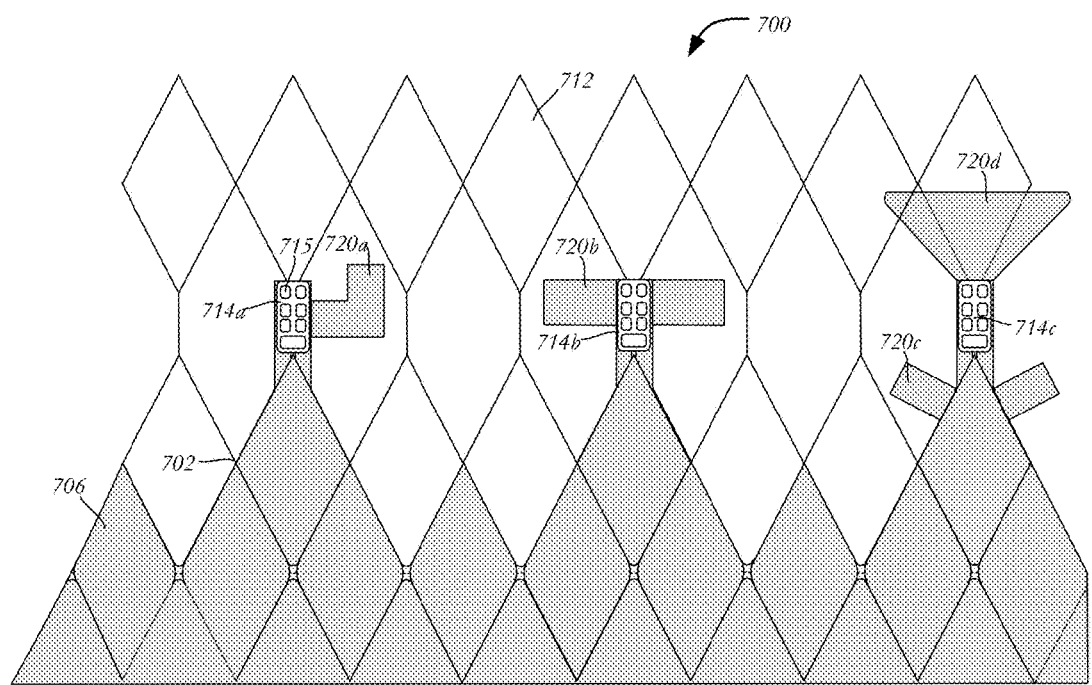
FIG. 7 is a highly schematic partial developed view of a prosthetic valve with a cuff having folding flaps adjacent commissure features.

In addition to tabs and/or segments formed on the leaflet, bulk and/or stiffness may be added adjacent the attachment regions of a leaflet by modifying the cuff. FIG. 7 illustrates one such example in which material is added to the cuff to limit the movement of a leaflet. Heart valve 700 includes stent 702 and cuff 706. For the sake of clarity, leaflets are not shown. Stent 702 may include one or more annular rows of cells 712 connected to one another and a plurality of spaced commissure features 714a,714b,714c to which attachment features of the leaflet may be secured via eyelets 715.

Cuff 706 may include a plurality of flaps adjacent commissure features 714 for added bulk. A first example is L-shaped flap 720a, which extends laterally from behind commissure feature 714a. Only a single L-shaped flap 720a is shown, though it will be understood that each commissure feature 714 may be flanked by two symmetric or dissimilar L-shaped flaps. Adjacent second commissure feature 714b are flaps 720b configured as rectangular segments projecting laterally away from the commissure feature. Diagonal flaps 720c and a triangular flap 720d are disposed adjacent commissure feature 714c. It will be understood that any combination of these flaps may be formed at any combination of commissure features 714 or at all of the commissure features. Additionally, it will be understood that flaps 720 may be integrally formed with cuff 706 or may be separately formed and subsequently attached to cuff 706 using sutures, adhesive or any other suitable coupling method.

Figure 8A:
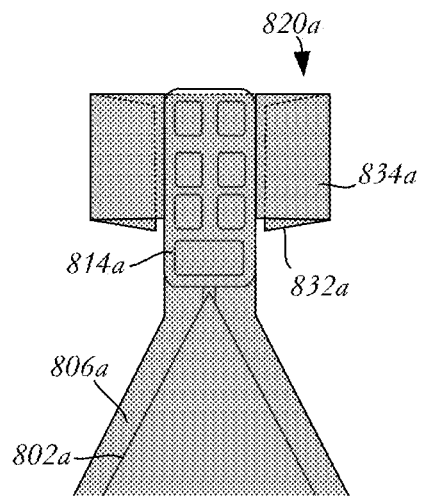
FIGS. 8A and 8B are highly schematic partial side views of folded and rolled cuff flaps, respectively.
Figure 8B:
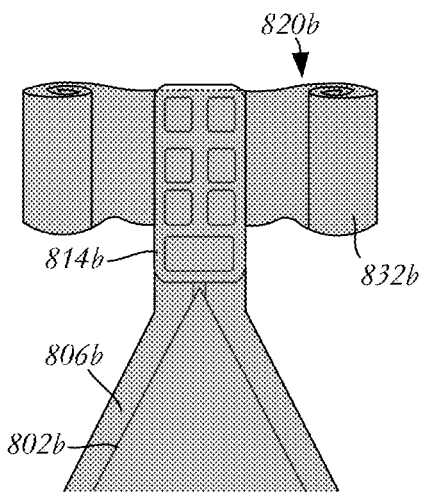

Two methods of using cuff flaps to redirect the leaflet motion are shown in FIGS. 8A and 8B. FIG. 8A shows stent 802a supporting cuff 806a. Stent 802a includes commissure feature 814a to which leaflets (not shown) would be attached to form a valve assembly. Cuff 806a includes two flaps 820a extending laterally from behind commissure feature 814a, each flap 820a being folded in half to form an inner panel 832a and outer panel 834a. Leaflets may be attached to commissure feature 814a through folded flaps 820a. When leaflets are attached to commissure feature 814a, folded flaps 820a may provide additional bulk and/or stiffness so as to limit the deflection of the leaflets. FIG. 8B illustrates a similar configuration including stent 802b, cuff 806b, commissure feature 814b and flaps 820b. Instead of being folded as shown in FIG. 8A, flaps 820b are rolled on themselves to form cushions 832b to pinch the leaflets together to redirect the leaflet motion. Finally, leaflets may be attached to commissure feature 814b through cushions 832b. It will be understood the above examples are merely illustrative and that other variations are possible. For example, flaps may be disposed over leaflets or in between leaflets and subsequently sutured together. Additionally, certain variation may not requiring suturing through the leaflet. Moreover, flaps may be attached before, during or after attachment of the leaflet attachment to a commissure feature.

Figure 9A:
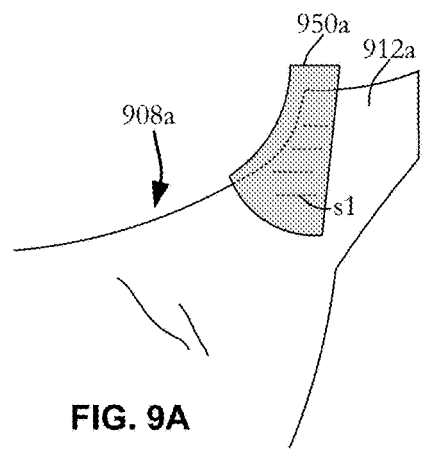
FIGS. 9A-E are various methods of suturing a swatch to a leaflet.
Figure 9B:
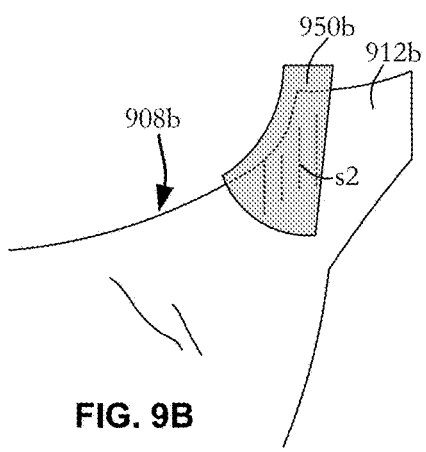
Figure 9C:
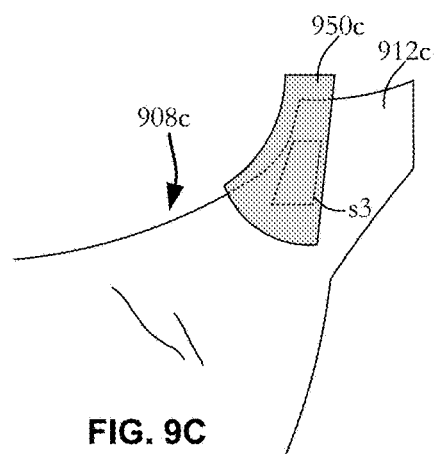
Figure 9D:
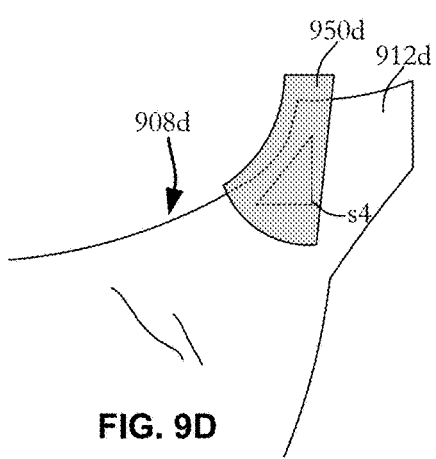
Figure 9E:
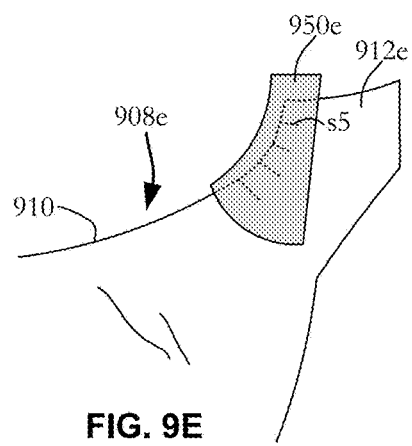

FIGS. 9A-E are various methods of suturing a swatch of material to a leaflet. In FIG. 9A, leaflet 908a at attachment region 912a via a plurality of horizontal sutures s1 spaced from one another in the longitudinal direction of the swatch. In FIG. 9B, swatch 950b is attached to leaflet 908b at attachment region 912b via a plurality of vertical sutures s2 spaced from one another in the width direction of the swatch. In FIG. 9C, swatch 950c is attached to leaflet 908c at attachment region 912c via a quadrilateral suture pattern s3. A triangular suture pattern s4 attaches swatch 950d to attachment region 912d of leaflet 902d in FIG. 9D. Finally, as shown in FIG. 9E swatch 950e is attached to attachment region 912e of leaflet 908e via a suture pattern s5 that includes a plurality of suture lines that are spaced from one another along free edge 910 of leaflet 908e. Each of the suture lines in suture pattern s5 may be substantially orthogonal to free edge 910. In these variations, several additional parameters may be adjusted to obtain the most beneficial configuration. For example, sutures may be spaced apart to avoid high stress concentrations. Moreover, sutures may also be spaced away from the free edge to reduce the risk of tears.

In operation, any of the embodiments of the prosthetic heart valve described above may be used to replace a native heart valve, such as the aortic valve. The prosthetic heart valve may be delivered to the desired site in a patient (e.g., near a native aortic annulus) in a collapsed condition using any suitable delivery device. The delivery device may be introduced into the patient using a transfemoral, transapical, transseptal, transradial, transaortic, transsubclavian or other percutaneous approach. Once the delivery device has reached the target site, the user may deploy the prosthetic heart valve. Upon deployment, the prosthetic heart valve expands into secure engagement within the native valve annulus. When the prosthetic heart valve has been properly positioned inside the heart, it works as a one-way valve, allowing blood to flow in one direction and preventing blood from flowing in the opposite direction. Swatches, leaflet tabs or cuff flaps may restrict the movement of a leaflet to reduce contact between the leaflet and other portions (e.g., stent and/or cuff) of the heart valve when opening and closing, thereby reducing the risk of abrasion of the leaflet.

Although the invention herein has been described with reference to particular embodiments, it is to be understood that these embodiments are merely illustrative of the principles and applications of the present invention. For example, a prosthetic heart valve may include individual swatches, leaflet tabs, cuff flap or any suitable combination of the three. It is therefore to be understood that numerous modifications may be made to the illustrative embodiments and that other arrangements may be devised without departing from the spirit and scope of the present invention as defined by the appended claims.

In some embodiments, a prosthetic heart valve includes a stent extending in a longitudinal direction and having a plurality of commissure features, a collapsed condition and an expanded condition; a valve assembly secured to the stent, the valve assembly including a cuff and a plurality of leaflets, each of the leaflets having a pair of attachment regions and a free edge extending between the attachment regions; and a deflection feature in an attachment region of a leaflet and configured and arranged to prevent the free edge of the leaflet from contacting at least one of the stent or the cuff.

In some examples, the deflection feature includes a swatch of material coupled to the attachment region, the material being selected from a group consisting of a fabric, a tissue and a polymer, and/or the swatch of material is folded over the free edges of two of the leaflets, and/or the swatch of material includes a pair of lobes joined to one another by a tailored neck, the tailored neck being folded over the free edges of the two leaflets, and/or the leaflet has an inner surface and an outer surface and the swatch of material includes two symmetric wings, each wing being coupled to one of the surfaces of the leaflet, and/or each wing has a quadrilateral shape, and/or the deflection feature includes an enlarged rectangular attachment region rolled on itself about an axis extending in the longitudinal direction to form a coil, and/or the deflection feature includes a leaflet tab connected to the attachment region of the leaflet, and/or the leaflet tab has a rectangular shape and is folded over the attachment region along a fold line extending substantially in the longitudinal direction, and/or the leaflet tab has a rectangular shape, the leaflet tab being folded on itself along a first fold line extending in a direction substantially orthogonal to the longitudinal direction and being folded over the attachment region along a second fold line extending substantially in the longitudinal direction, and/or the leaflet tab has equally an L-shape and is folded over the attachment region along fold lines extending substantially in the longitudinal direction and in a direction substantially orthogonal to the longitudinal direction, and/or the leaflet tab has generally an S-shape and is folded over the attachment region along fold lines extending substantially in the longitudinal direction and in a direction substantially orthogonal to the longitudinal direction, and/or the deflection feature includes a flap coupled to the cuff adjacent to each of the commissure features, and/or the flap has generally an L-shape, a rectangular shape, or a triangular shape, and/or the flap is folded on itself, and/or the flap is rolled on itself to form a cushion, and/or the flap is coupled to at least one of the plurality of leaflets.

In some embodiments, a prosthetic heart valve includes a stent having a collapsed condition and an expanded condition, the stent having a plurality of commissure features; a valve assembly secured to the stent, the valve assembly including a cuff and a plurality of leaflets, each of the leaflets having a pair of attachment regions and a free edge extending between the attachment regions; and at least one of a swatch of material, a leaflet tab and a cuff flap disposed adjacent the attachment regions and configured and arranged to prevent the free edge of one of the plurality of leaflets from contacting at least one of the stent or the cuff.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve, comprising:
a stent extending in a longitudinal direction and having a plurality of struts forming cells and a plurality of commissure features, each commissure feature being attached to selected struts at proximal and distal ends thereof;
a plurality of leaflets, each of the leaflets having a pair of attachment regions, each being attached to a commissure feature, and a free edge extending between the attachment regions; and
a cuff annularly disposed on a surface of the stent, the cuff extending between a first end and a second end, and having a main body, a rectangular portion disposed over each of the commissure features of the stent, and a deflection feature adjacent each of the rectangular portions near the second end of the cuff, the deflection feature being folded on itself, and entirely disposed on a luminal surface of the stent, and the deflection feature being configured and arranged to prevent the free edge of the leaflet from contacting at least one of the stent, and a calcium nodule.

2. The prosthetic heart valve according to claim 1, wherein the deflection feature includes an L-shape flap.

3. The prosthetic heart valve according to claim 1, wherein the deflection feature includes parallelogram-shaped flap.

4. The prosthetic heart valve according to claim 1, wherein the deflection feature includes a triangular flap.

5. The prosthetic heart valve according to claim 1, wherein the deflection feature is rolled on itself to form a cushion.

* * * * *